United States Patent
Igarashi

(10) Patent No.: US 11,458,240 B2
(45) Date of Patent: Oct. 4, 2022

(54) BIOLOGICAL COMPONENT COLLECTION SYSTEM WITH INTERNAL PRESSURE SENSOR AND METHOD

(71) Applicant: TERUMO KABUSHIKI KAISHA, Shibuya-ku (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 189 days.

(21) Appl. No.: 16/649,062

(22) PCT Filed: Sep. 27, 2018

(86) PCT No.: PCT/JP2018/035874
§ 371 (c)(1),
(2) Date: Mar. 19, 2020

(87) PCT Pub. No.: WO2019/065812
PCT Pub. Date: Apr. 4, 2019

(65) Prior Publication Data
US 2021/0162112 A1    Jun. 3, 2021

(30) Foreign Application Priority Data
Sep. 28, 2017  (JP) .............................. JP2017-187337

(51) Int. Cl.
*A61M 1/38*  (2006.01)
*A61M 1/36*  (2006.01)

(52) U.S. Cl.
CPC ............ *A61M 1/3693* (2013.01); *A61M 1/38* (2013.01); *A61M 2202/0415* (2013.01); *A61M 2205/12* (2013.01); *A61M 2205/3331* (2013.01)

(58) Field of Classification Search
CPC ................ A61M 1/38; A61M 2205/12; A61M 2205/3331
See application file for complete search history.

(56) References Cited

U.S. PATENT DOCUMENTS

| 4,637,813 A | 1/1987 | DeVries |
| 5,178,603 A | 1/1993 | Prince |
| (Continued) | | |

FOREIGN PATENT DOCUMENTS

| EP | 0214803 A2 | 3/1987 |
| EP | 2233164 | 9/2010 |
| (Continued) | | |

OTHER PUBLICATIONS

International Search Report and Written Opinion, PCT/JP2018/035874, dated Dec. 10, 2018, 14 pages.

(Continued)

*Primary Examiner* — Bradley R Spies
(74) *Attorney, Agent, or Firm* — Sheridan Ross P.C.

(57) ABSTRACT

A blood component collection system, which is one form of a biological component collection system, is equipped with a centrifugal separation device and a biological component collection device. The biological component collection device comprises a pressed soft portion pressed by a load detecting unit. The centrifugal separation device includes a collection and returning pump, and a control unit having an internal pressure computation unit which calculates a circuit internal pressure of the biological component collection device on the basis of a detection value of the load detecting unit. The internal pressure computation unit performs a zero reset process of setting a pressure value corresponding to the detection value of the load detecting unit, so as to become zero at each instance of a predetermined timing at which the collection and returning pump is stopped.

16 Claims, 16 Drawing Sheets

(56) References Cited

U.S. PATENT DOCUMENTS

| | | | |
|---|---|---|---|
| 5,536,237 | A | 7/1996 | Prince et al. |
| 6,280,406 | B1 | 8/2001 | Dolecek et al. |
| 6,491,656 | B1 | 12/2002 | Morris |
| 10,352,950 | B2 | 7/2019 | Ochiai |
| 10,413,653 | B2 | 9/2019 | Case et al. |
| 10,758,664 | B2 | 9/2020 | Igarashi |
| 10,758,665 | B2 | 9/2020 | Igarashi et al. |
| 10,773,013 | B2 | 9/2020 | Igarashi |
| 10,780,212 | B2 | 9/2020 | Igarashi |
| 10,881,765 | B2 | 1/2021 | Igarashi |
| 10,960,128 | B2 | 3/2021 | Igarashi et al. |
| 2002/0028155 | A1 | 3/2002 | Dolecek et al. |
| 2002/0107468 | A1 | 8/2002 | Chevallet et al. |
| 2010/0152013 | A1 | 6/2010 | Eberle et al. |
| 2010/0292628 | A1 | 11/2010 | Powers et al. |
| 2011/0152055 | A1 | 6/2011 | Pittinger et al. |
| 2015/0238677 | A1 | 8/2015 | Akita et al. |
| 2016/0243300 | A1 | 8/2016 | Nackaerts et al. |
| 2017/0007323 | A1* | 1/2017 | Leo ........................ A61B 34/10 |
| 2019/0038197 | A1 | 2/2019 | Igarashi |
| 2019/0046710 | A1 | 2/2019 | Kusters et al. |
| 2019/0231949 | A1 | 8/2019 | Igarashi |
| 2019/0290822 | A1 | 9/2019 | Igarashi |
| 2019/0290830 | A1 | 9/2019 | Igarashi |
| 2020/0030505 | A1 | 1/2020 | Igarashi |
| 2020/0164135 | A1 | 5/2020 | Igarashi |
| 2020/0197583 | A1 | 6/2020 | Igarashi |
| 2020/0222614 | A1 | 7/2020 | Igarashi |
| 2020/0316282 | A1 | 10/2020 | Igarashi |

FOREIGN PATENT DOCUMENTS

| | | |
|---|---|---|
| EP | 3228341 | 10/2017 |
| JP | 2017-143970 | 8/2017 |
| WO | WO 96/40322 | 12/1996 |
| WO | WO 2004/061399 | 7/2004 |
| WO | WO 2008/121120 | 10/2008 |
| WO | WO 2011/084348 | 7/2011 |
| WO | WO 2014/105755 | 7/2014 |
| WO | WO 2016/057364 | 4/2016 |
| WO | WO 2017/142003 | 8/2017 |
| WO | WO 2018/051982 | 3/2018 |
| WO | WO 2018/230155 | 12/2018 |
| WO | WO 2018/230156 | 12/2018 |
| WO | WO 2018/230545 | 12/2018 |

OTHER PUBLICATIONS

International Search Report and Written Opinion for International (PCT) Patent Application No. PCT/JP2018/035871, dated Apr. 8, 2019, 25 pages.

International Search Report and Written Opinion for International (PCT) Patent Application No. PCT/JP2019/041298, dated Jan. 23, 2020, 16 pages.

International Search Report and Written Opinion for International (PCT) Patent Application No. PCT/JP2019/041299, dated Jan. 23, 2020, 16 pages.

International Search Report and Written Opinion for International (PCT) Patent Application No. PCT/JP2019/041300, dated Jan. 23, 2020, 16 pages.

Official Action for U.S. Appl. No. 16/362,477, dated Feb. 4, 2020, 17 pages.

Notice of Allowance for U.S. Appl. No. 16/362,477, dated Aug. 13, 2020, 6 pages.

Official Action for U.S. Appl. No. 16/362,519, dated Feb. 4, 2020, 16 pages.

Notice of Allowance for U.S. Appl. No. 16/362,519, dated Aug. 11, 2020, 6 pages.

Official Action for U.S. Appl. No. 16/620,933, dated Aug. 20, 2020, 10 pages.

Notice of Allowance for U.S. Appl. No. 16/620,933, dated Nov. 30, 2020, 6 pages.

Official Action for U.S. Appl. No. 16/668,435, dated Jan. 24, 2020, 10 pages.

Official Action for U.S. Appl. No. 16/668,435, dated May 15, 2020, 9 pages.

Official Action for U.S. Appl. No. 16/668,435, dated Sep. 21, 2020, 13 pages.

Notice of Allowance for U.S. Appl. No. 16/668,435, dated Feb. 2, 2021, 5 pages.

Official Action for U.S. Appl. No. 16/668,750, dated Jan. 24, 2020, 17 pages.

Notice of Allowance for U.S. Appl. No. 16/668,750, dated Jul. 21, 2020, 9 pages.

Official Action for U.S. Appl. No. 16/668,572, dated Jan. 24, 2020, 17 pages.

Notice of Allowance for U.S. Appl. No. 16/668,572, dated Jul. 23, 2020, 6 pages.

Official Action (with English translation) for Japan Patent Application No. 2020-510130, dated Feb. 8, 2022, 8 pages.

* cited by examiner

BIOLOGICAL COMPONENT COLLECTION SYSTEM WITH INTERNAL PRESSURE SENSOR AND METHOD

TECHNICAL FIELD

The present invention relates to a biological component collection system and a circuit internal pressure acquisition method.

BACKGROUND ART

In blood donation in recent years, in addition to whole blood collection in which whole blood is collected from blood donors, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining components are returned again into the donor's body.

For example, in Japanese Laid-Open Patent Publication No. 2013-514863 (PCT), a blood component collection system is disclosed in which blood platelets are collected by centrifugally separating whole blood that is extracted from a blood donor. Such a blood component collection system includes a blood collection circuit set, which forms a circuit through which blood or blood components to be treated flow, and a centrifugal separation device (blood component separating device) on which the blood collection circuit set is mounted.

The blood collection circuit set is equipped with a plurality of bags for accommodating a blood collection line having a blood collection needle, a band-shaped channel (separator) into which whole blood is introduced, and the blood components, etc., and a cassette connected through a plurality of tubes to the bags. A plurality of flow paths, including a line for introducing blood from a blood donor, a line for transferring the blood components into a bag, a blood returning line for returning uncollected blood components to the donor, etc., are formed in the cassette. When used, the cassette is mounted in a mounting unit disposed in the blood component separating device.

SUMMARY OF INVENTION

In the blood component collection system, in order to ascertain whether or not the blood component separation device is operating properly, it is necessary to measure and monitor the pressure (circuit internal pressure) inside the blood collection circuit. In addition, it is desirable that the circuit internal pressure can be measured accurately. Similar problems also occur in biological component collection systems other than blood component collection systems.

The present invention has been devised taking into consideration the aforementioned problems, and has the object of providing a biological component collection system, and a circuit internal pressure acquisition method, which are capable of accurately measuring the circuit internal pressure.

In order to achieve the above-described objects, the present invention is a biological component collection system, comprising a separation device having a load detecting unit, and adapted to separate a biological component from a liquid containing at least one biological component, and a biological component collection device configured to be attachable to the separation device and having a flow path formed in the interior thereof, wherein the biological component collection device comprises a pressed soft portion forming one part of the flow path, and which is pressed by the load detecting unit in order to measure an internal pressure of the flow path when the separation device is in operation, the separation device comprises a collection and returning pump, and a control unit having an internal pressure computation unit which calculates a circuit internal pressure of the biological component collection device on the basis of a detection value of the load detecting unit, and the internal pressure computation unit performs a zero reset process of setting a pressure value corresponding to the detection value of the load detecting unit, so as to become zero at each instance of a predetermined timing at which the pump is stopped.

According to the biological component collection system which is constituted in the manner described above, the zero reset process (initialization) is performed to set the pressure value corresponding to the detection value of the load detecting unit, so as to become zero at each instance of the predetermined timing at which the collection and returning pump is stopped. Therefore, it is possible to enhance the measurement accuracy of the circuit internal pressure. More specifically, although the reaction force of the pressed soft portion that is pressed by the load detecting unit changes (decreases) over time, since the pressure value is returned to zero at each instance of the predetermined timing at which the pump is stopped, it is possible to reduce the amount of change over time in the reaction force of the pressed soft portion. Consequently, it is possible to reduce measurement errors due to a decrease in the reaction force over time, and to measure the circuit internal pressure with high measurement accuracy.

The separation device may perform a collection operation of collecting in the biological component collection device the liquid containing at least one biological component from a donor, and a returning operation of returning an unnecessary biological component to the donor, and the internal pressure computation unit may perform the zero reset process while stopping the pump in order to switch between the collection operation and the returning operation.

In accordance with such a configuration, in the case that the respective cycle times of the collection operation and the returning operation are comparatively short, the zero reset process is executed at the switching timing to stop the pump, and therefore the zero reset process is efficient. Further, by performing the zero reset process during a relatively short time interval, it is possible to reduce the amount of change over time in the reaction force of the pressed soft portion, and to measure the circuit internal pressure with higher accuracy.

The separation device may perform a collection operation of collecting in the biological component collection device the liquid containing at least one biological component from a donor, the control unit may stop the pump at least one time during a period of the collection operation, and the internal pressure computation unit may perform the zero reset process while stopping the pump during the period of the collection operation.

In accordance with such a configuration, even in the case that the cycle time of the collection operation is comparatively long, since the zero reset process is performed at each of the predetermined time intervals, the circuit internal pressure can be accurately measured.

The time during which the pump is stopped at the predetermined timing may be greater than or equal to 2 seconds.

In accordance with this feature, the circuit internal pressure can be reliably returned to 0 mmHg (or a pressure equivalent thereto), and therefore, the effectiveness of the zero reset process can be enhanced.

The time during which the pump is stopped at the predetermined timing may be less than or equal to 5 seconds.

In accordance with this feature, it is possible to prevent the overall processing time period of the biological component collection system from becoming longer than necessary.

Further, the present invention is a circuit internal pressure acquisition method for measuring a circuit internal pressure of a biological component collection device with a flow path formed in the interior thereof together with being attached to a separation device having a load detecting unit, and adapted to separate a biological component from a liquid containing at least one biological component, wherein the biological component collection device is equipped with a pressed soft portion forming one part of the flow path, the internal pressure acquisition method comprising a pump stopping step of stopping a collection and returning pump at a predetermined timing during operation of the separation device, and an internal pressure calculation step of calculating a circuit internal pressure of the biological component collection device on the basis of a detection value of the load detecting unit, wherein, in the internal pressure calculation step, a zero reset process is performed to set a pressure value corresponding to the detection value of the load detecting unit, so as to become zero at each instance of the predetermined timing.

The circuit internal pressure acquisition method may further comprise performing a collection operation of collecting in the biological component collection device the liquid containing at least one biological component from a donor, and a returning operation of returning an unnecessary biological component to the donor, and in the internal pressure calculation step, the zero reset process may be performed while stopping the pump in order to switch between the collection operation and the returning operation.

In accordance with the biological component collection system and the circuit internal pressure acquisition method of the present invention, it is possible to accurately measure the circuit internal pressure.

DESCRIPTION OF EMBODIMENTS

Preferred embodiments of a biological component collection device and a biological component collection system according to the present invention will be presented and described in detail below with reference to the accompanying drawings.

Figure 1:
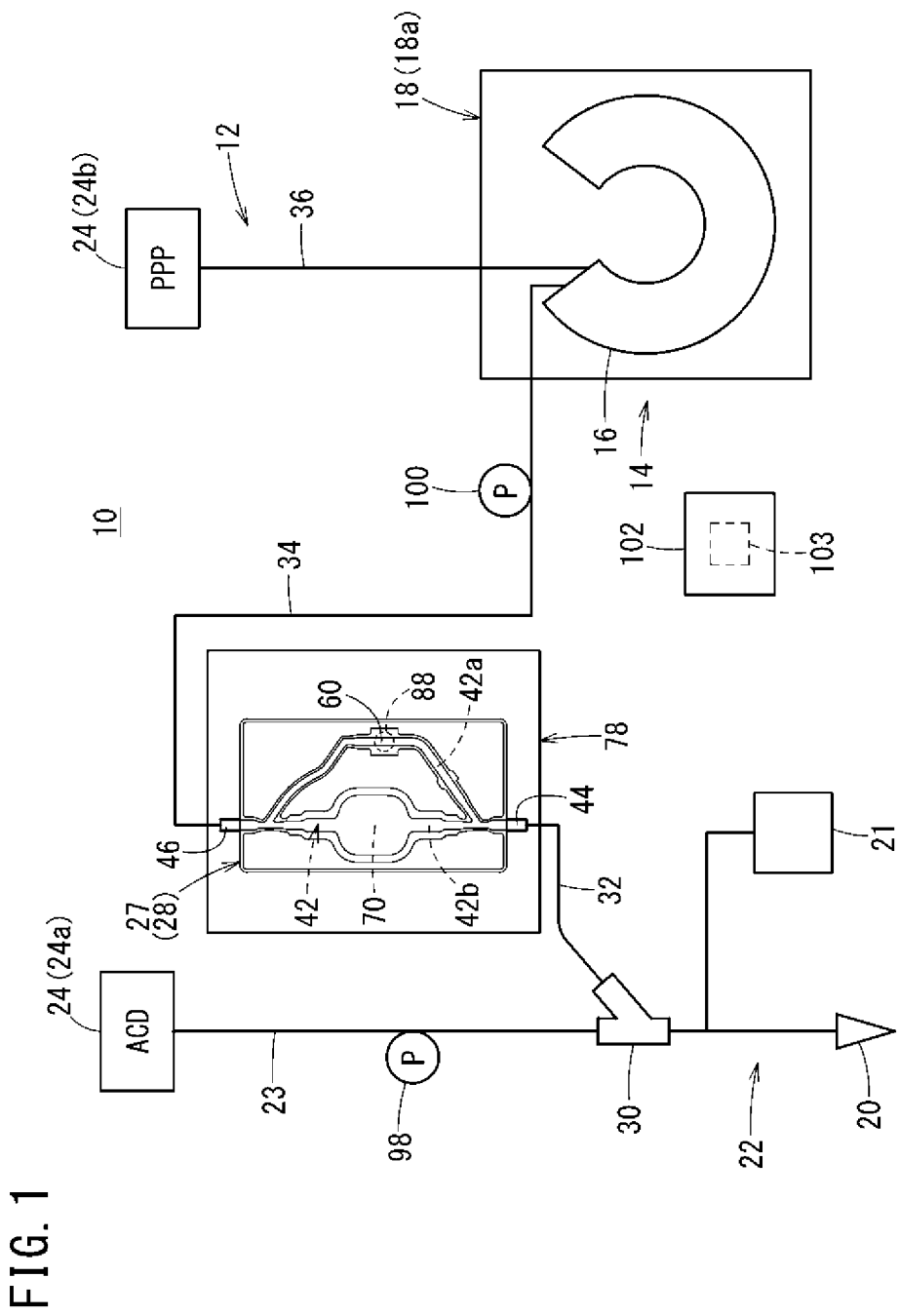
FIG. 1 is a schematic diagram of a blood component collection system according to an embodiment of the present invention.

As shown in FIG. 1, a blood component collection system 10, which is an embodiment of the biological component collection system, is constituted as a blood apheresis system, in which blood (whole blood) is continuously extracted from a blood donor and the blood is continuously extracted outside the body, whereby a specific blood component (in the present embodiment, plasma (platelet poor plasma: PPP)) is collected and the remaining blood components are returned to the blood donor. In the present embodiment, the blood is defined as "a liquid containing at least one biological component".

First, an outline description will be given of the blood component collection system 10 shown in FIG. 1. The blood component collection system 10 is equipped with a blood collection circuit set 12 for enabling storage and flow of blood components therein, and centrifugal separation device 14 (one form of a blood component separation device or a separation device) that applies a centrifugal force to the blood collection circuit set 12. The blood collection circuit set 12 includes a blood treatment unit 16 to which there is introduced whole blood that is removed from the blood donor, and the whole blood is centrifugally separated into a plurality of blood components. The centrifugal separation device 14 is equipped with a centrifuge unit 18 having a rotor 18a for applying a centrifugal force to the blood treatment unit 16. The blood treatment unit 16 is capable of being mounted in the centrifuge unit 18.

The blood collection circuit set 12 is discarded every time that it is used in order to prevent contamination and ensure sanitation. The blood collection circuit set 12 includes a blood collection and blood returning unit 22 having a blood collection needle 20 and an initial flow blood collection bag 21, a blood treatment unit 16, a plurality of bags 24, and a cassette 28 which is one form of a biological component collection device 27. The plurality of bags 24 include an ACD solution bag 24a containing an ACD solution which is an anticoagulant, and a PPP bag 24b for storing the plasma (platelet poor plasma).

The blood collection and blood returning unit 22 is connected to the ACD solution bag 24a and the cassette 28 via a tube connector 30. The ACD solution bag 24a is connected to the tube connector 30 via an ACD solution transfer tube 23.

The cassette 28 is connected to the blood collection and blood returning unit 22 via a donor side tube 32, and is also connected to the blood treatment unit 16 via a treatment unit side tube 34. The blood treatment unit 16 is attached to the centrifuge unit 18 (rotor 18a) of the centrifugal separation device 14, and is configured in the form of a container in which blood can be introduced therein, flow therethrough, and flow out therefrom. The PPP bag 24b is connected to the blood treatment unit 16 via a PPP transfer tube 36.

Figure 2:
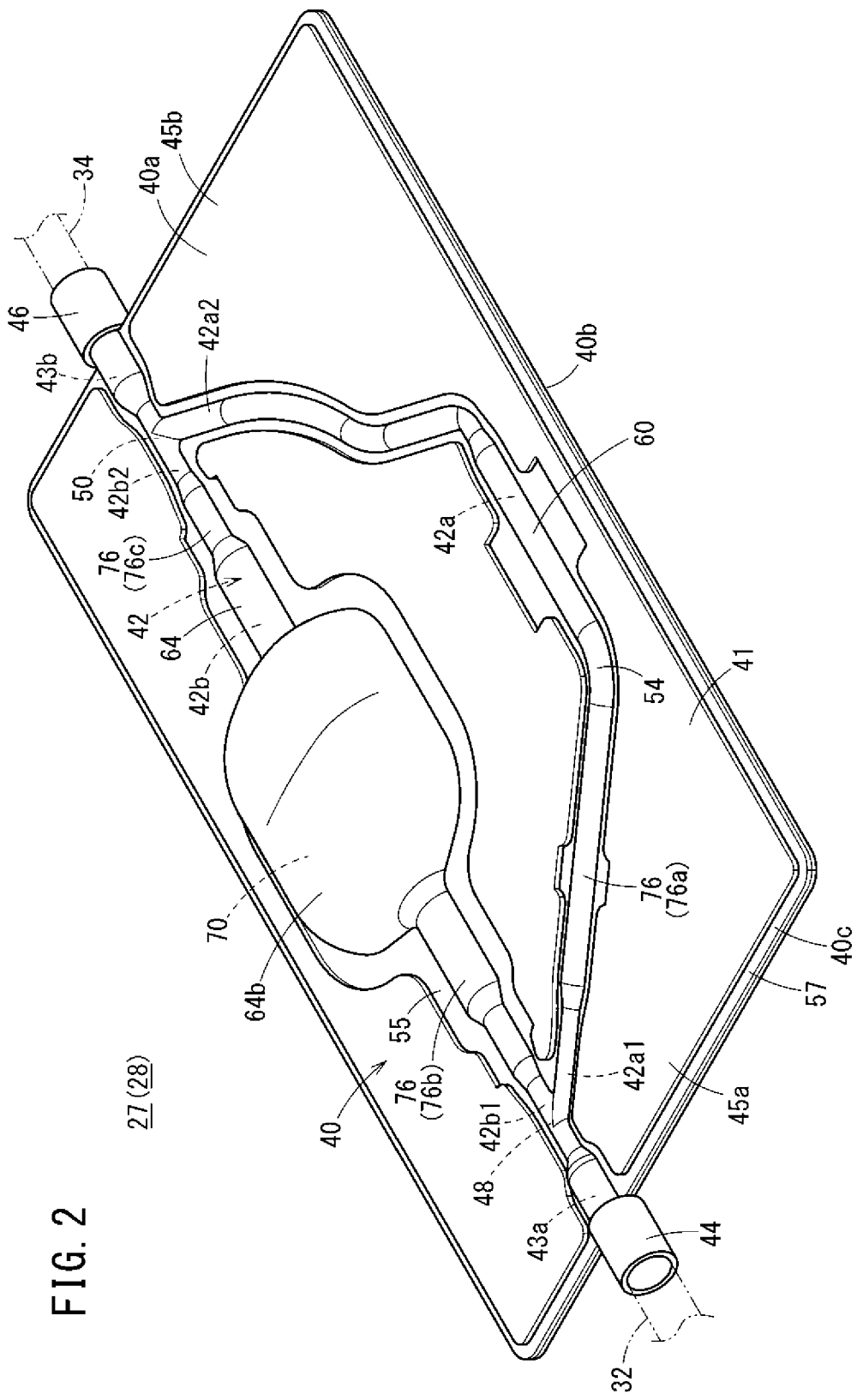
FIG. 2 is a perspective view of a biological component collection device.

As shown in FIG. 2, the cassette 28 is provided with a cassette body 40 in which a flow path 42 is formed. The cassette body 40 is formed in a rectangular shape as viewed in plan. The cassette body 40 is formed of a soft material. For the soft material that constitutes the cassette body 40, the same material is used over the entirety of the cassette body 40. Moreover, the cassette body 40 may be constituted from a plurality of different materials. More specifically, the cassette body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

A flow path 42 is formed between the first sheet 40a and the second sheet 40b. Fusion bonding (high frequency fusion bonding, thermal fusion bonding, etc.) is used as the means for joining the first sheet 40a and the second sheet 40b. The first sheet 40a and the second sheet 40b may also be joined together by another joining means (adhesion or the like). Further, a first port member 44 and a second port member 46, which are made of a hard material (for example, polypropylene, polycarbonate, or the like), are disposed on an outer peripheral edge portion 40c of the cassette body 40.

The first port member 44 is provided at a first end portion 45a, which is one longitudinal end portion of the rectangular cassette body 40, and is connected to a first port 43a provided on one end side of the flow path 42. The second port member 46 is provided at a second end portion 45b, which is another longitudinal end portion of the cassette body 40, and is connected to a second port 43b provided on the other end side of the flow path 42. The donor side tube 32 and the treatment unit side tube 34 are connected respectively to the port members 44, 46.

The flow path 42 formed in the cassette body 40 includes a first line 42a through which blood flows when the centrifugal separation device 14 is in operation, and a second line 42b in which a filter member 70 is disposed. A first end portion 42a1 of the first line 42a and a first end portion 42b1 of the second line 42b are connected via a first coupling member 48. A second end portion 42a2 of the first line 42a, and a second end portion 42b2 of the second line 42b are connected via a second coupling member 50. The first line 42a and the second line 42b extend at least partially in parallel with each other. The first coupling member 48 and the second coupling member 50 each constitute parts of the flow path 42.

In the cassette body 40, seal members 55 in the form of fusion-bonded locations are formed along the flow path 42 on both sides of the flow path 42. Further, a seal member 57 is formed along the outer peripheral edge portion 40c, on the outer peripheral edge portion 40c of the cassette body 40.

In the cassette body 40, even if there is no positive pressure acting within the flow path 42, the wall portions that form the flow path 42 bulge in convex shapes in the thickness direction of the cassette 28 on both side surfaces of the cassette body 40. Accordingly, the flow path 42 is a flow path which is opened in its natural state. When pressed by an external force, the wall portions can be elastically deformed in directions to close the flow path 42 at the pressed location thereof.

The cassette body 40 comprises a first line forming member 54 that forms the first line 42a, and a second line forming member 64 that forms the second line 42b.

The first line forming member 54 includes a pressed soft portion 60 made of a soft material. In order to measure the internal pressure of the flow path 42 during operation of the centrifugal separation device 14, in a state (hereinafter referred to as a "cassette attached state") in which the cassette 28 is attached to the centrifugal separation device 14, the pressed soft portion 60 is a site that is pressed by a later-described load detecting unit 88 which is installed in the centrifugal separation device 14. The interior of the pressed soft portion 60 constitutes a part of the flow path 42. The pressed soft portion 60 bulges out in the thickness direction of the cassette body 40, from a sheet surface 41 (base surface) of the cassette body 40.

The second line forming member includes a filter accommodating unit 64b. Although not shown in detail, a filter member 70 in the form of a sheet mesh is disposed inside the filter accommodating unit 64b for the purpose of removing clotted blood or blood clumps contained within the blood or the blood components.

On the cassette 28, there are provided a plurality of clamp action members 76 (76a to 76c) on which a plurality of clamps 72 (72a to 72c) (see FIG. 3), which act as flow path opening/closing mechanisms, are provided in the centrifugal separation device 14. When the cassette 28 is installed in the centrifugal separation device 14, the clamp action members 76 abut against or are placed in facing relation to their corresponding clamps 72. More specifically, the clamp action member 76a is disposed at a location forming an end portion of the first line 42a in the cassette 28 on the side of the first port member 44. The clamp action members 76b, 76c are disposed respectively at locations forming both end portions of the second line 42b.

Moreover, the flow path structure formed in the cassette 28, and the number and arrangement of the bags 24 that are provided are not limited to the configurations shown and described above, but may be modified in accordance with the type of blood components to be collected, the method of use, and the like.

In a method for manufacturing the cassette 28 having the above-described configuration, there are included a molding step in which the first sheet 40a and the second sheet 40b are superimposed on each other, and the first sheet 40a and the second sheet 40b are fusion bonded together so as to form the flow path 42 between the first sheet 40a and the second sheet 40b, to thereby mold the cassette 28 equipped with the cassette body 40, and a sterilization step of sterilizing the cassette 28 obtained by the aforementioned molding step.

In the molding step, for example, a sheet-shaped material is fed out from two material rolls on which there are wound, respectively, sheet materials that serve as the materials for the first sheet 40a and the second sheet 40b, and the assembly components (the filter member 70, the port members 44, 46) are supplied together therewith to a joining device such as a high-frequency fusion bonding device or the like. The joining device is equipped with upper and lower molds, and by carrying out blow molding while the two sheet-shaped materials are joined together with the assembly components, the cassette 28 is molded with the flow path 42 formed therein. In this case, the tubes 32, 34 may be connected at the time that the cassette 28 is molded in the joining device.

In the sterilization step, the entirety of the blood collection circuit set 12 including the plurality of bags 24 (ACD solution bag 24a, etc.) may be sterilized. Consequently, the blood collection circuit set 12 can be sterilized efficiently.

In FIG. 1, the centrifugal separation device 14 is a device that is used repeatedly during blood component collection, and is provided, for example, in a medical facility, a blood collection vehicle, or the like. The centrifugal separation device 14 is equipped with the centrifuge unit 18 having the rotor 18a, and a cassette mounting unit 78 configured in a manner so that the cassette 28 of the blood collection circuit set 12 is capable of being attached thereto.

Figure 3:
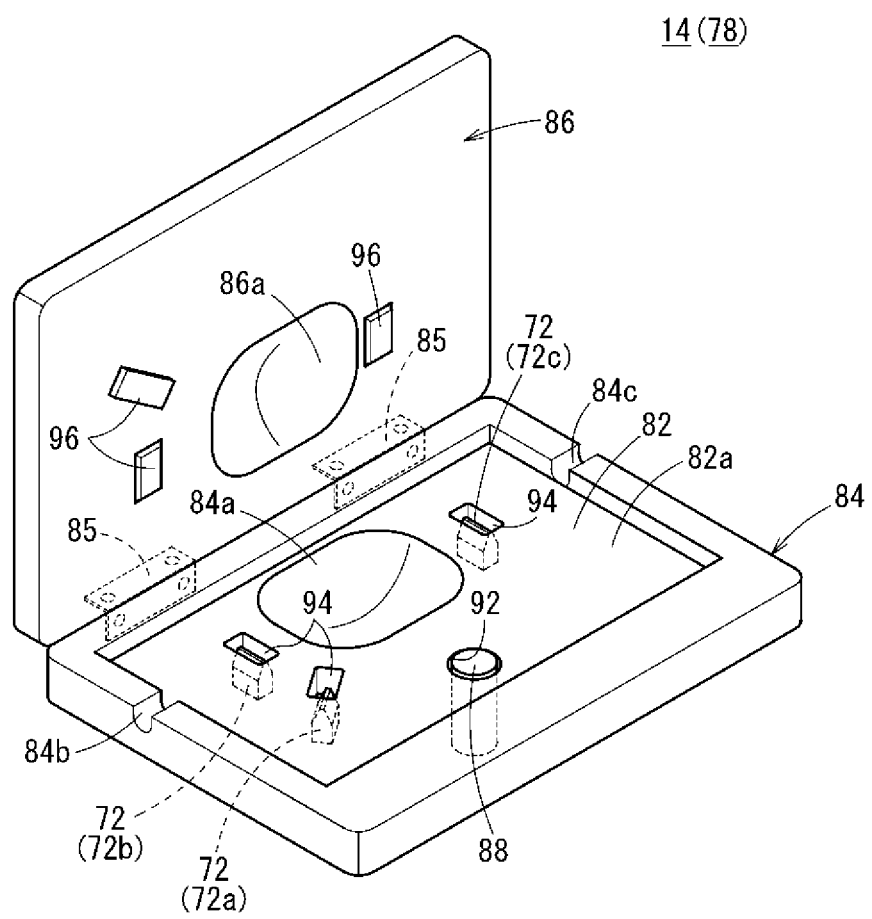
FIG. 3 is a perspective view of a cassette mounting unit.

As shown in FIG. 3, the cassette mounting unit 78 includes an attachment base 84 having a cassette mounting groove 82 formed therein, a lid 86 which can be opened and closed and is configured in a manner to cover the attachment base 84 when closed, a plurality of clamps 72 configured to be capable of pressing the clamp action members 76 of the cassette 28, and a load detecting unit 88 capable of pressing the pressed soft portion 60 (see FIG. 2) of the cassette 28.

A first port arrangement groove 84b into which the first port member 44 of the cassette 28 can be arranged, and a second port arrangement groove 84c into which the second port member 46 of the cassette 28 can be arranged are provided on the outer peripheral portion of the attachment base 84. The first port arrangement groove 84b and the second port arrangement groove 84c are in communication with the cassette mounting groove 82.

The lid 86 is connected in a rotatable manner to the attachment base 84 via a hinge 85. When the lid 86 is closed with the cassette 28 being held in the cassette mounting groove 82 of the attachment base 84, the cassette 28 is sandwiched between the attachment base 84 and the lid 86. On the attachment base 84 and the lid 86, there are respectively provided concave portions 84a, 86a in which the filter accommodating unit 64b of the cassette 28 can be received. Consequently, the cassette 28 is appropriately retained between the attachment base 84 and the lid 86, while also preventing the filter accommodating unit 64b from being crushed. Further, the concave portions 84a, 86a prevent the filter accommodating unit 64b from bulging excessively.

The load detecting unit 88 is inserted into a through hole 92 provided in the attachment base 84, together with being exposed in the cassette mounting groove 82. An upper surface of the load detecting unit 88 protrudes from a bottom surface 82a of the cassette mounting groove 82. The load detecting unit 88 is constituted, for example, by a load cell.

The plurality of clamps 72 (72a to 72c) are capable of being advanced and retracted in the thickness direction of the cassette 28 in a state in which the cassette 28 is retained in the cassette mounting groove 82, and are disposed corresponding to the arrangement of the plurality of clamp action members 76 (76a to 76c) provided on the cassette 28. The plurality of clamps 72 are capable of pressing the plurality of clamp action members 76, respectively, via a plurality of holes 94 that open on a bottom surface 82a of the cassette mounting groove 82. When closed, a plurality of projections 96 are provided on the lid 86 at positions corresponding to the plurality of holes 94 (clamps 72).

At a time that the clamp action members 76 are not being pressed by the clamps 72, in a state in which the cassette 28 is mounted in the cassette mounting unit 78, the flow paths inside the clamp action members 76 are opened. When the clamps 72 protrude from the holes 94 and press the clamp action members 76, the flow paths inside the clamp action members 76 are closed. In addition, when the clamps 72 are retracted, due to the elastic restorative force of (the clamp action members 76 of) the cassette body 40, the clamp action members 76 are restored to their original shape, and the flow paths inside the clamp action members 76 are opened.

As shown in FIG. 1, the centrifugal separation device 14 includes an ACD solution transfer pump 98 which acts on the ACD solution transfer tube 23, and a collection and returning pump 100 which acts on the treatment unit side tube 34 that is connected to the cassette 28. The ACD solution transfer pump 98 is a pump that transfers the ACD solution from the ACD solution bag 24a to the cassette 28 and the blood treatment unit 16 via the ACD solution transfer tube 23. The collection and returning pump 100 is a pump that transfers blood from the blood donor to the blood treatment unit 16, and together therewith, transfers blood from the blood treatment unit 16 back to the blood donor. The ACD solution transfer pump 98 and the collection and returning pump 100 are constituted, for example, by a roller pump or a finger pump.

The centrifugal separation device 14 further includes a control unit 102 adapted to control the centrifuge unit 18, the cassette mounting unit 78, and the pumps 98, 100. The operations of the aforementioned plurality of clamps 72 and the collection and return ng pump 100 are controlled by the control unit 102. The control unit 102 includes an internal pressure computation unit 103 which, when the centrifugal separation device 14 is in operation, acquires (calculates) the circuit internal pressure of the blood collection circuit set 12, on the basis of the load detected by the load detecting unit 88 (see FIG. 3).

Next, operations of the blood component collection system 10 according to the present embodiment, which is configured in the manner described above, will be described.

As a preparation (set-up) for collecting blood components from a blood donor using the blood component collection system 10 shown in FIG. 1, the blood collection circuit set 12 is attached to the centrifugal separation device 14. More specifically, the cassette 28 is mounted in the cassette mounting unit 78, and the blood treatment unit 16 is attached to the rotor 18a. On the other hand, the blood collection needle 20 pierces and is inserted into the blood donor.

Figure 4:
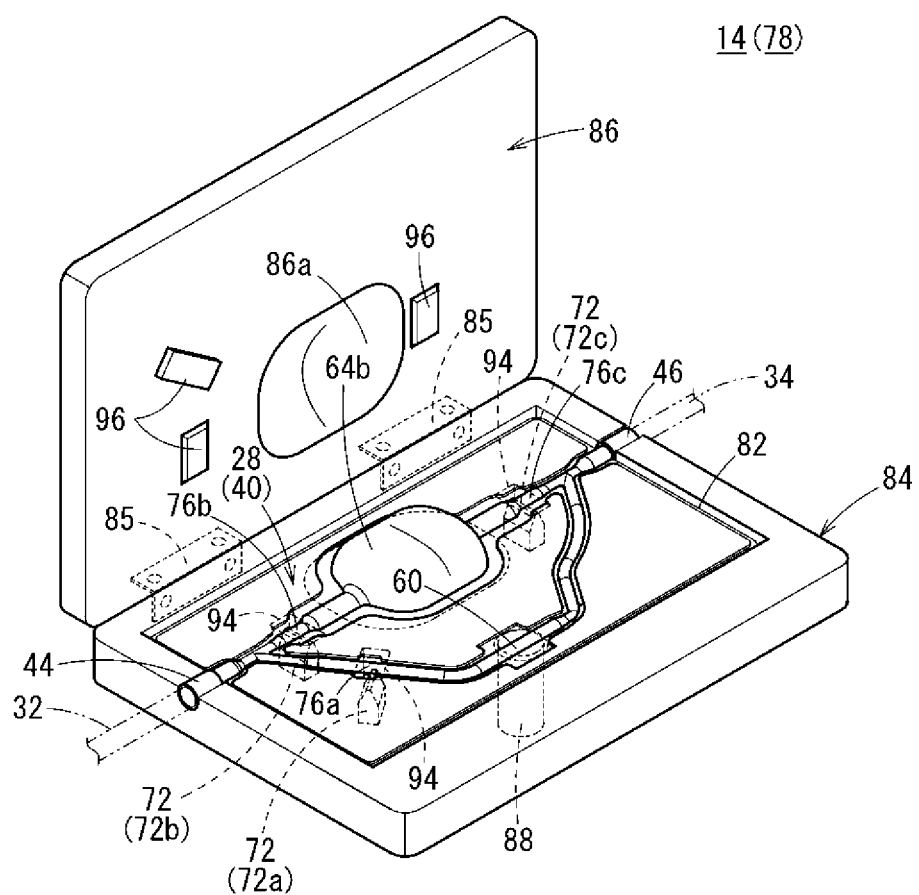
FIG. 4 is a perspective view of a cassette mounting unit in a state with the biological component collection device placed therein.

When the cassette 28 is mounted in the cassette mounting unit 78, as shown in FIG. 4, at first, the cassette 28 is mounted in the cassette mounting groove 82. In addition, by closing the lid 86, the cassette 28 is placed in a state of being held between the lid 86 and the attachment base 84. As a result, the pressed soft portion 60 of the cassette 28 is pressed by the load detecting unit 88 and is placed in a state of being slightly elastically deformed. Further, the plurality of clamp action members 76 of the cassette 28 are placed in facing relation with respect to the plurality of clamps 72.

When a command is issued by operation of a user with respect to the centrifugal separation device 14 shown in FIG. 1 in order to initiate operations, in the centrifugal separation device 14, under the action of the ACD solution transfer pump 98, priming with the ACD solution is carried out. More specifically, at a stage at which it is detected by a non-illustrated line sensor disposed outside of the cassette 28 that the ACD solution has arrived in the immediate vicinity of the flow path 42, priming by the ACD solution is terminated.

Next, by rotating the rotor 18a, the centrifugal separation device 14 applies a centrifugal force to the blood treatment unit 16 that is attached to the rotor 18a, and together therewith, by operation of the collection and returning pump 100, blood (whole blood) from the blood donor is extracted and introduced into the blood treatment unit 16 (blood collection operation). By the centrifugal force that accompanies rotation of the rotor 18a, the blood introduced into the blood treatment unit 16 is separated into red blood cells (concentrated red blood cells), a buffy coat, and plasma (platelet poor plasma).

The plasma that is separated in the blood treatment unit 16 is introduced into the PPP bag 24b via the PPP transfer tube 36. After completion of the centrifugal separation process, the remaining blood components (the red blood cells and the buffy coat) are returned to the blood donor (returning operation). At this time, since foreign substances such as blood clumps and the like contained within the remaining blood components are trapped by the filter member 70 provided in the second line 42b of the cassette 28, any risk of such foreign matter being returned to the blood donor can be reduced. The collection operation and the returning operation described above are repeated a plurality of times.

During operation of the blood component collection system 10, the clamps 72 (see FIG. 3) of the centrifugal separation device 14 are operated in the following manner.

Figure 5:
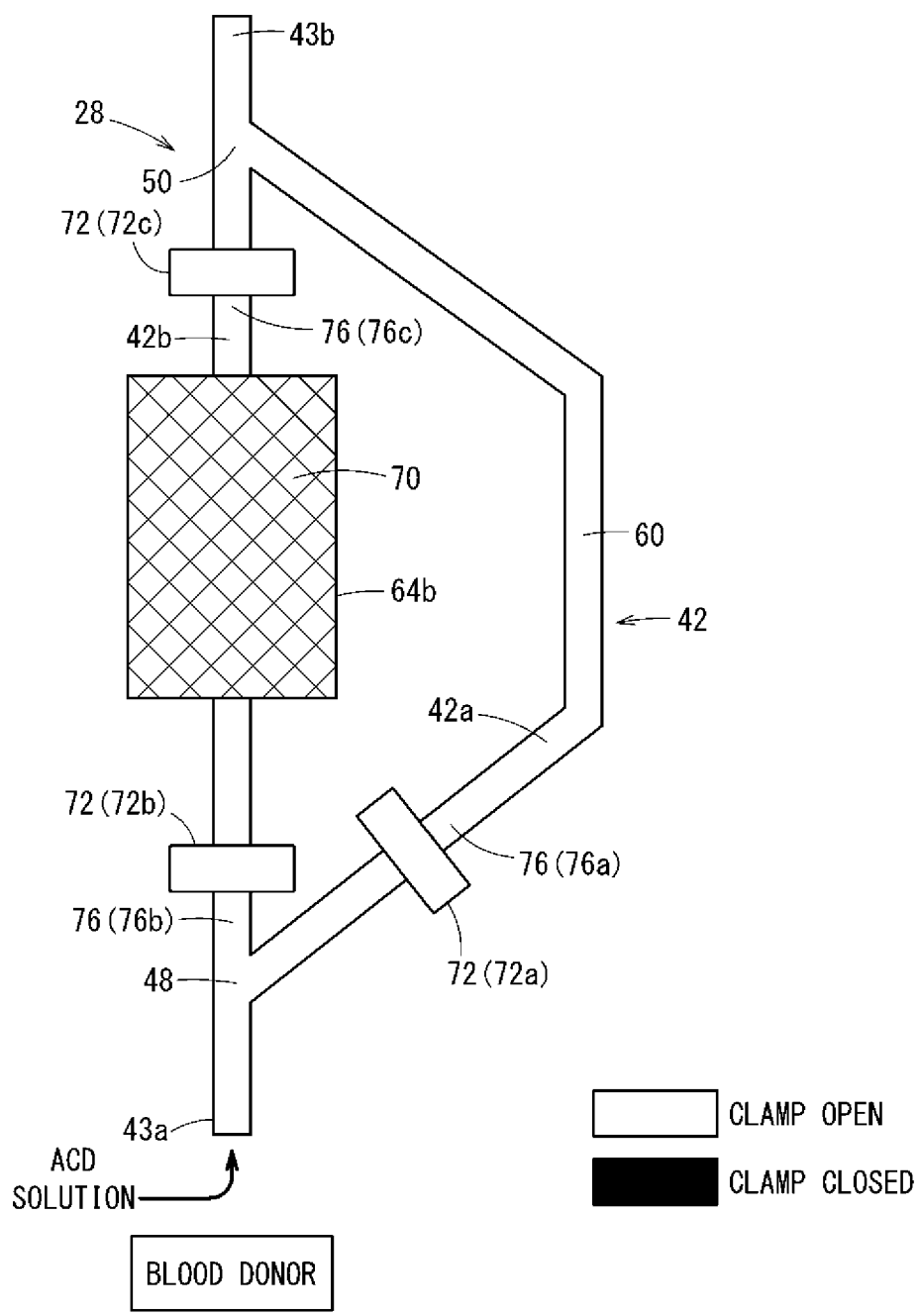
FIG. 5 is a first explanatory diagram illustrating the operation of clamps.

As shown in FIG. 5, when priming is carried out by the ACD solution, the clamps 72a to 72c are opened. In addition, in this state, priming by the ACD solution is terminated at a stage at which it is detected by a non-illustrated line sensor outside the cassette 28 in the immediate vicinity of the first port 43a that the ACD solution has arrived in close proximity to the first port 43a.

Figure 6:
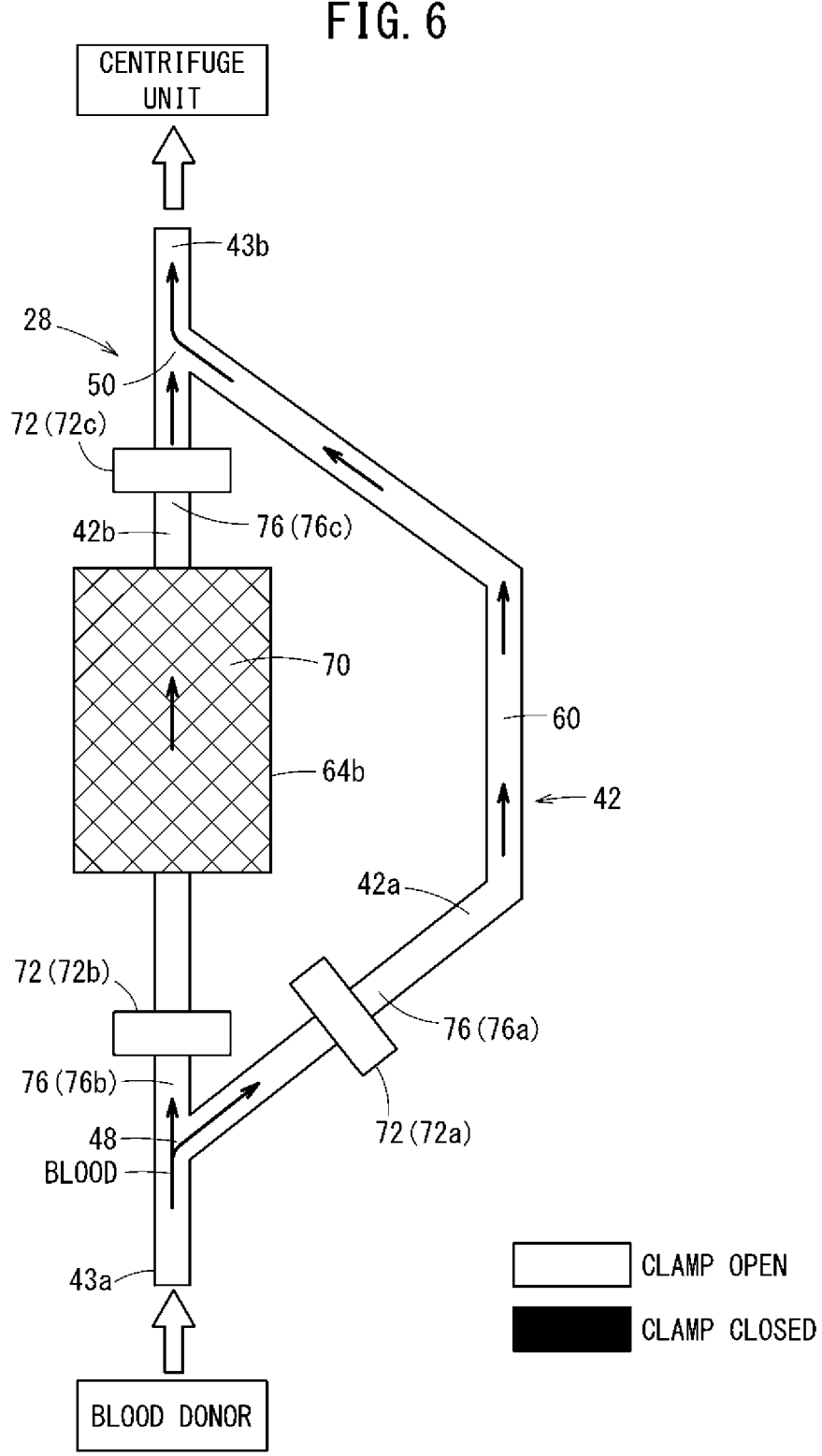
FIG. 6 is a second explanatory diagram illustrating the operation of clamps.

Next, as shown in FIG. 6, when blood collection is carried out for the first time, blood from the blood donor is introduced into the flow path 42 of the cassette 28, and all of the air inside the cassette 28 is pushed out by the blood into the blood treatment unit 16. Such a collection operation is performed by driving the collection and returning pump 100 (see FIG. 1) under the control of the control unit 102.

Figure 7:
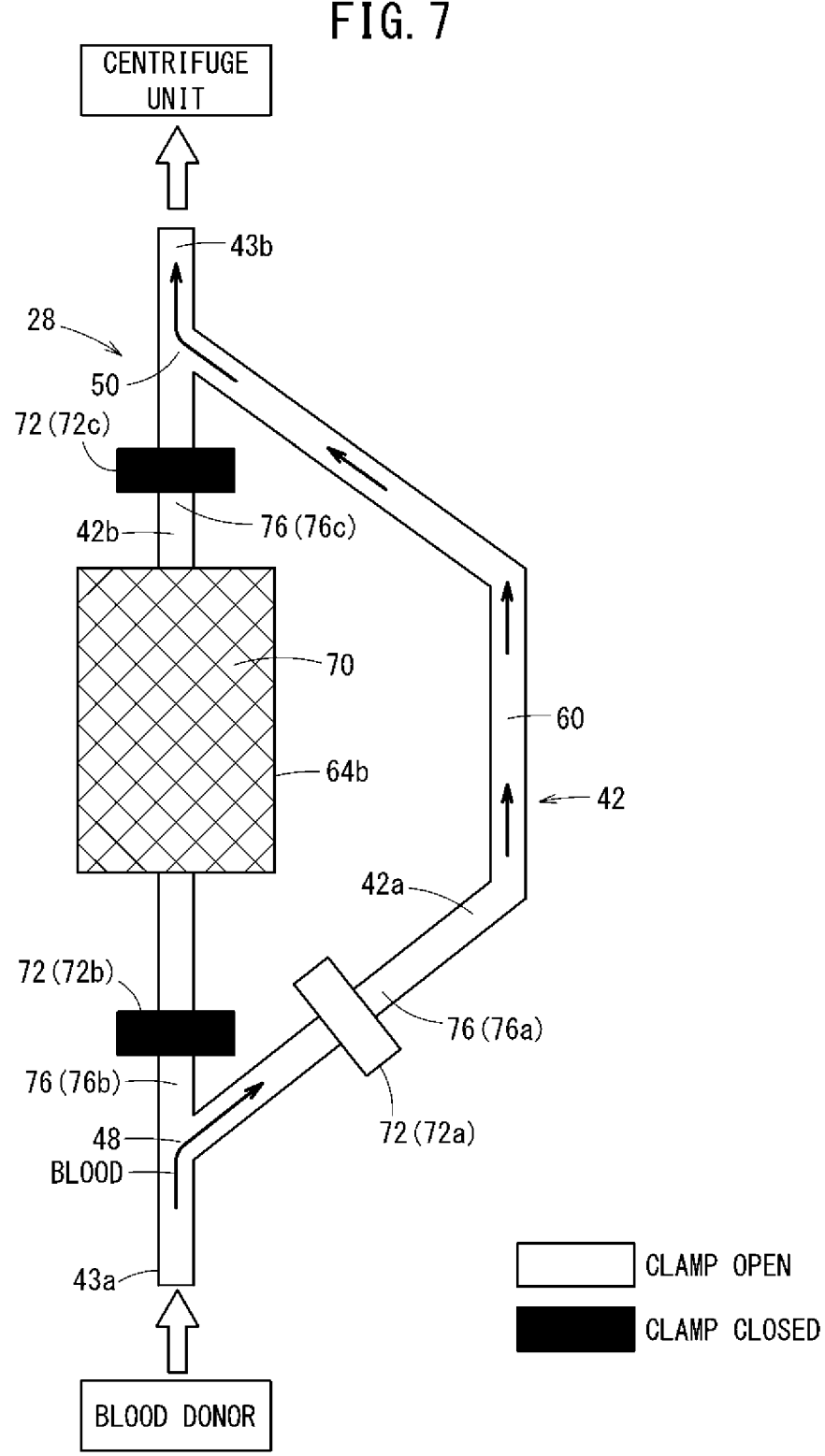
FIG. 7 is a third explanatory diagram illustrating the operation of clamps.

During the course of the initial blood collection, as shown in FIG. 7, by closing the clamps 72b and 72c, the second line 42b is closed. Consequently, a negative pressure is prevented from acting on the filter accommodating unit 64b and blocking the filter accommodating unit 64b.

Figure 8:
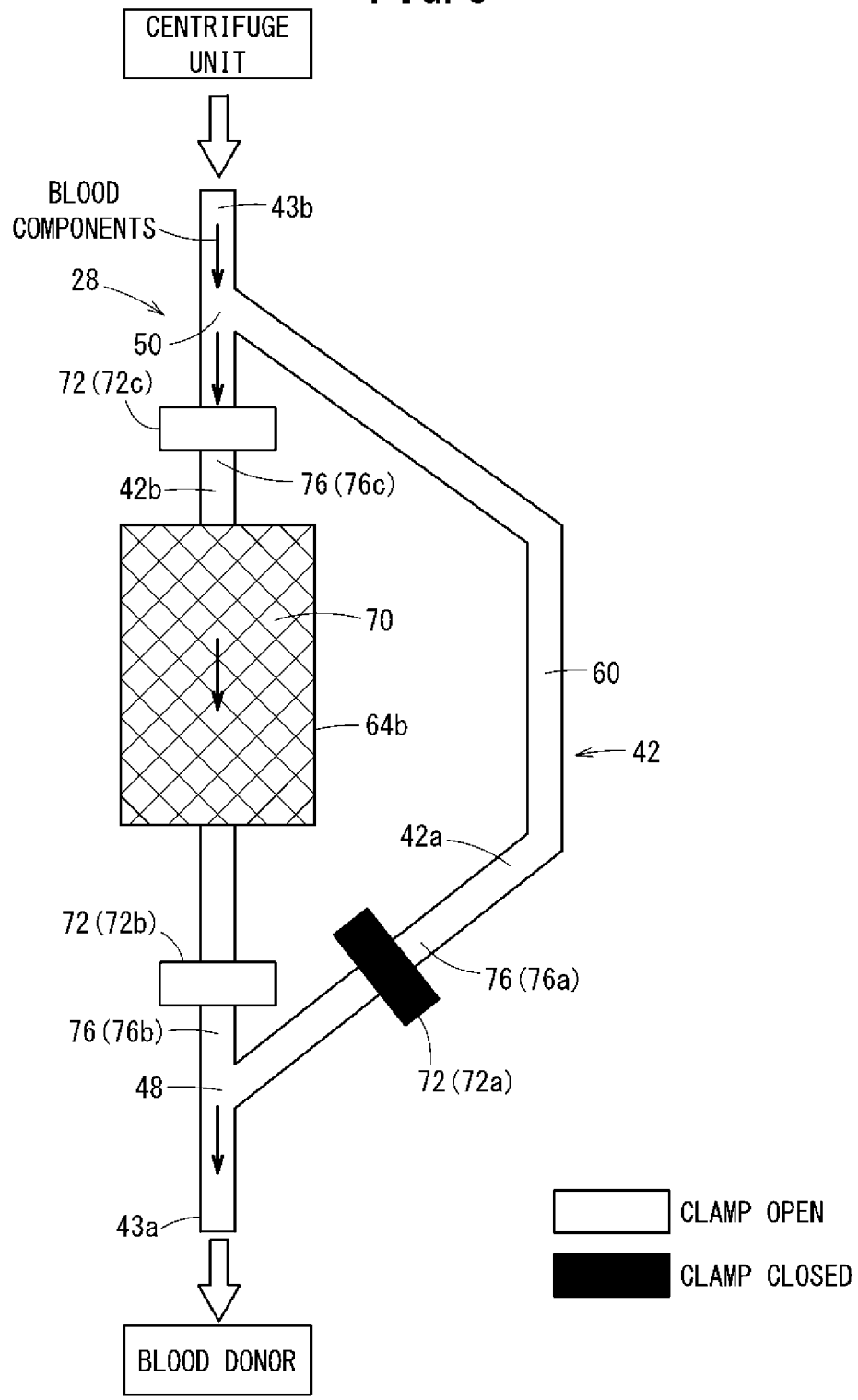
FIG. 8 is a fourth explanatory diagram illustrating the operation of clamps.

Next, when return of the blood components to the blood donor is carried out, as shown in FIG. 8, the clamp 72a is closed, and the clamps 72b and 72c are opened. Thus, the first line 42a is closed, whereas the second line 42b is opened. Accordingly, when the blood components pass through the filter member 70, clotted blood contained within the blood components is trapped in the filter member 70. Since the first line 42a is closed, clotted blood cannot be returned to the donor via the first line 42a. Such a returning operation is performed by driving the collection and returning pump 100 (see FIG. 1) under the control of the control unit 102. When the operations are switched from the collection operation shown in FIG. 7 to the returning operation shown in FIG. 8 (a period from the end of the collection operation until the start of the next returning operation), the collection and returning pump 100 is stopped.

Figure 9:
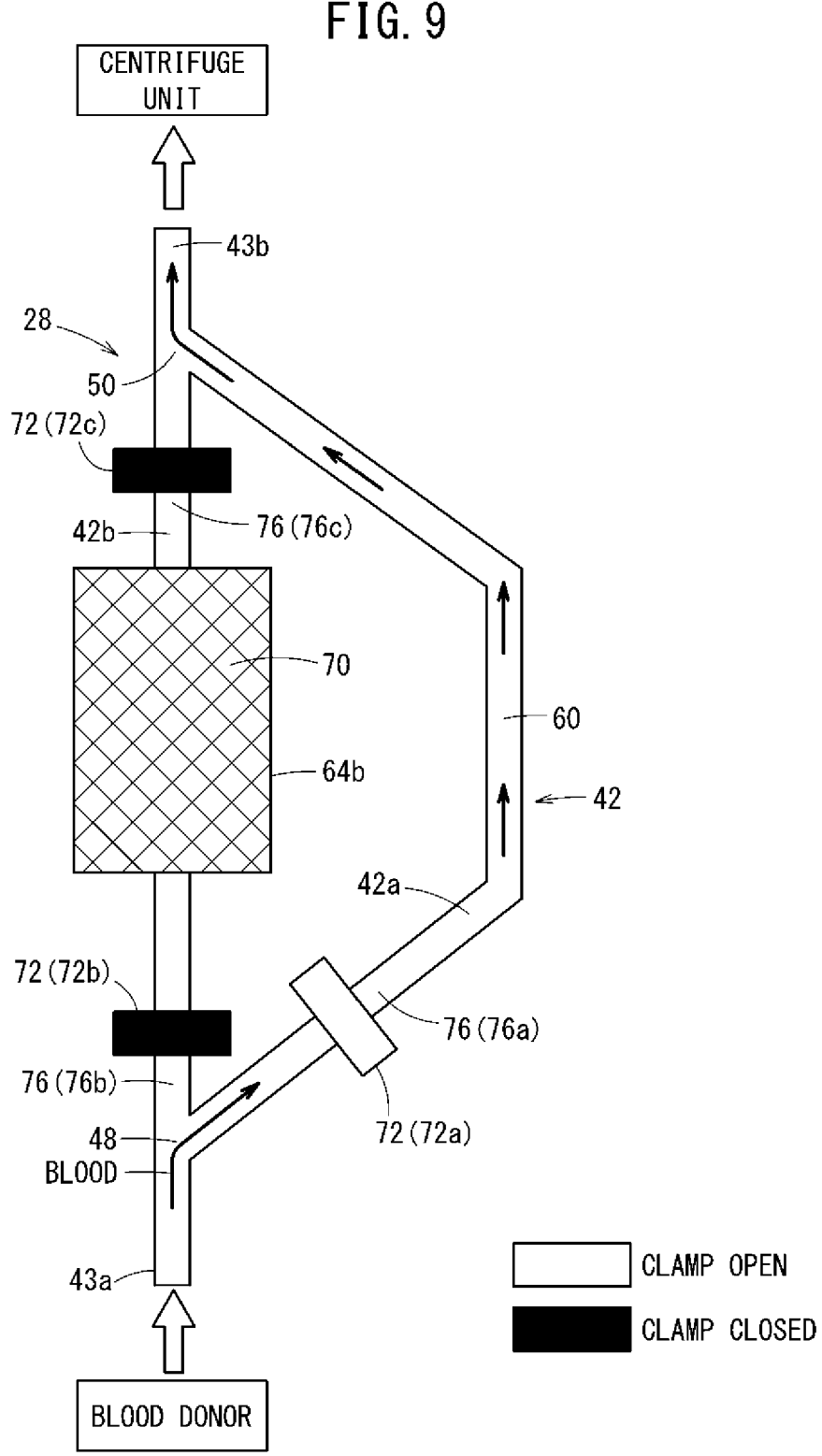
FIG. 9 is a fifth explanatory diagram illustrating the operation of clamps.

Next, when second and subsequent blood collections are carried out, as shown in FIG. 9, the clamps 72b and 72c are closed, and the clamp 72a is opened. Thus, the second line 42b is closed, whereas the first line 42a is opened. Accordingly, from among the first line 42a and the second line 42b, blood is transferred via only the first line 42a to (the centrifuge unit 18 of) the blood treatment unit 16. When the operations are switched from the returning operation shown in FIG. 8 to the collection operation shown in FIG. 9 (a period from the end of the returning operation until the start of the next collection operation), the collection and returning pump 100 is stopped. After such a collection operation, the returning operation (see FIG. 8) is performed again. The collection operation and the returning operation are repeated a plurality of times. When the collection operation and the returning operation are switched, the collection and returning pump 100 is stopped at each instance thereof.

In addition, when return of the blood is performed for the last time, the clamp 72a is closed, and the clamps 72b and 72c are opened (see FIG. 8).

Next, a circuit internal pressure acquisition method according to the present embodiment in which the blood component collection system 10 is used will be described.

Figure 10:
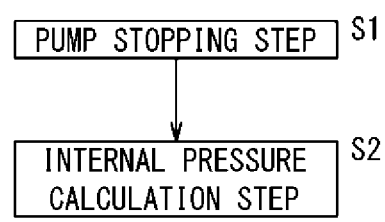
FIG. 10 is a flowchart of a circuit internal pressure acquisition method according to an embodiment of the present invention.

As shown in FIG. 10, the circuit internal pressure acquisition method includes a pump stopping step S1 of stopping the collection and returning pump 100 at a predetermined timing during operation of the centrifugal separation device 14, and an internal pressure calculation step S2 of calculating a circuit internal pressure of the cassette 28 on the basis of a detection value of the load detecting unit 88. In the internal pressure calculation step S2, a zero reset process is performed to set a pressure value corresponding to the detection value of the load detecting unit 88, so as to become zero at each instance of a predetermined timing at which the collection and returning pump 100 is stopped.

More specifically, the centrifugal separation device 14 measures the circuit internal pressure (negative pressure and positive pressure) on the basis of the load detected by the load detecting unit 88 (see FIG. 3). The circuit internal pressure is calculated by the internal pressure computation unit 103 (see FIG. 1) of the centrifugal separation device 14. The measured circuit internal pressure, for example, ranges from −300 to 500 mmHg.

Figure 11A:
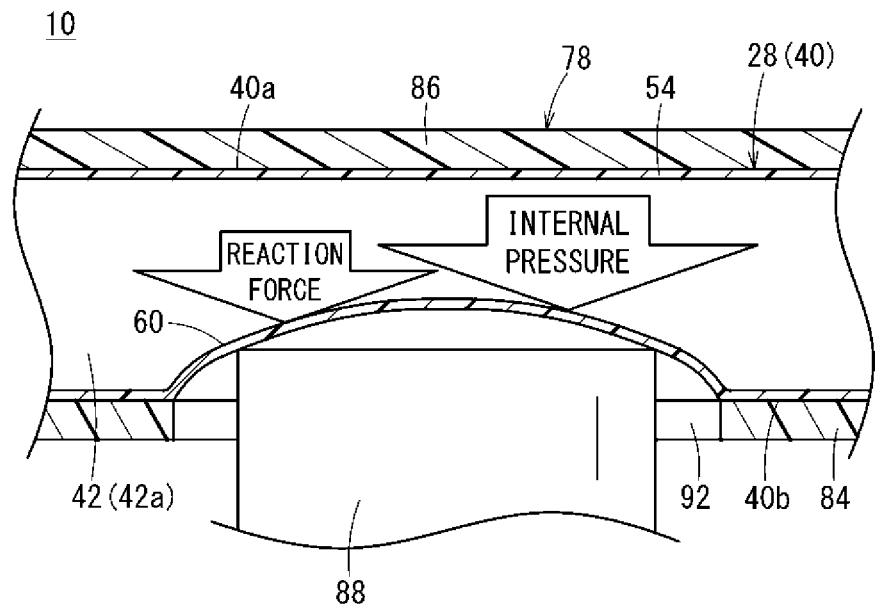
FIG. 11A is a view for explaining the detection of loads at a positive pressure.
Figure 11B:
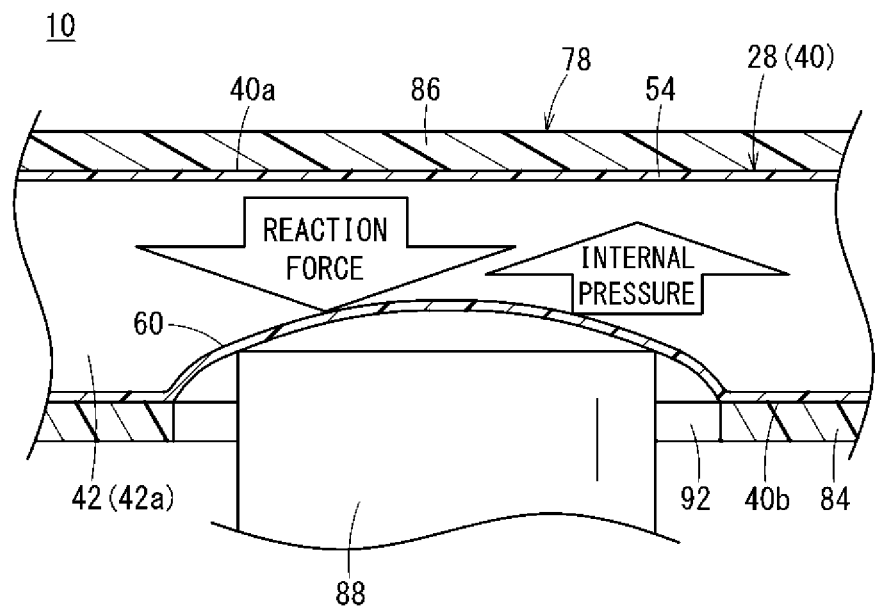
FIG. 11B is a view for explaining the detection of loads at a negative pressure.

A load, which is obtained by summing the internal pressure (circuit internal pressure) of the first line 42a through which the blood flows, and the reaction force of the pressed soft portion 60 (the restorative force accompanying deformation of the pressed soft portion 60), is detected by the load detecting unit 88. In the case that the circuit internal pressure is a positive pressure, as shown in FIG. 11A, the load that acts on the load detecting unit 88 (the pressing force from the pressed soft portion 60) is obtained simply by adding the circuit internal pressure and the reaction force. On the other hand, in the case that the circuit internal pressure is a negative pressure, as shown in FIG. 11B, the load that acts on the load detecting unit 88 is obtained simply by subtracting the absolute value of the circuit internal pressure from the reaction force.

Figure 12:
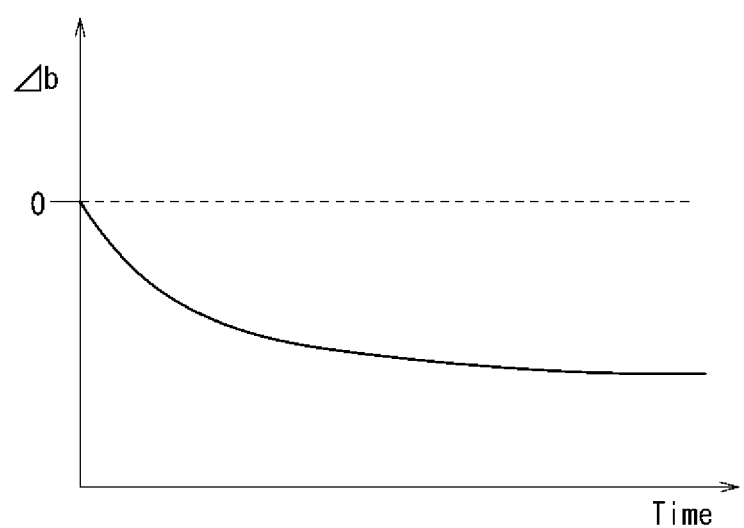
FIG. 12 is a diagram for explaining a decrease in a reaction force occurring over time.

As shown in FIG. 12, the reaction force of the pressed soft portion 60 decreases over time. In FIG. 12, there is shown an image of a temporal change (Δb) of the reaction force of the pressed soft portion 60 in the case that the initial reaction force of the pressed soft portion 60 is 0. The reason that the reaction force of the pressed soft portion 60 decreases over time in the foregoing manner is due to the fact that creep is generated accompanying continuation of a state in which the pressed soft portion 60 is pressed by the load detecting unit 88. Accordingly, when a fixed value that does not change over time is used as the reaction force of the pressed soft portion 60, the measurement accuracy of the circuit internal pressure is lowered. If the amount of change in the reaction force over time is stable, the amount of change can be predicted and is capable of being corrected. However, in actuality, if manufacturing conditions or the like differ for each of the cassettes 28, the amount of change in the reaction force over time varies significantly. For this reason, with a correction based on such a prediction, it is difficult for an effective correction to be made.

Thus, in the circuit internal pressure measurement method according to the present invention, a zero reset process of setting a pressure value corresponding to the detection value of the load detecting unit 88 is executed, so as to become zero at each instance of a predetermined timing at which the collection and returning pump 100 is stopped. More specifically, according to the present embodiment, the zero reset process is performed while the collection and returning pump 100 is stopped in order to switch between the collection operation and the returning operation. In this case, the time period during which the collection and returning pump 100 is stopped is preferably greater than or equal to 2 seconds and less than or equal to 5 seconds, and more preferably, is greater than or equal to 2.5 seconds and less than or equal to 3.5 seconds (on the order of 3 seconds). Because the flow path 42 inside the cassette 28 is an open system with respect to the blood donor via the donor side tube 32, the circuit is opened accompanying stoppage of the collection and returning pump 100. Therefore, while the collection and returning pump 100 is stopped, the circuit internal pressure returns to 0 mmHg (or a pressure in the vicinity of 0 mmHg).

Figure 13:
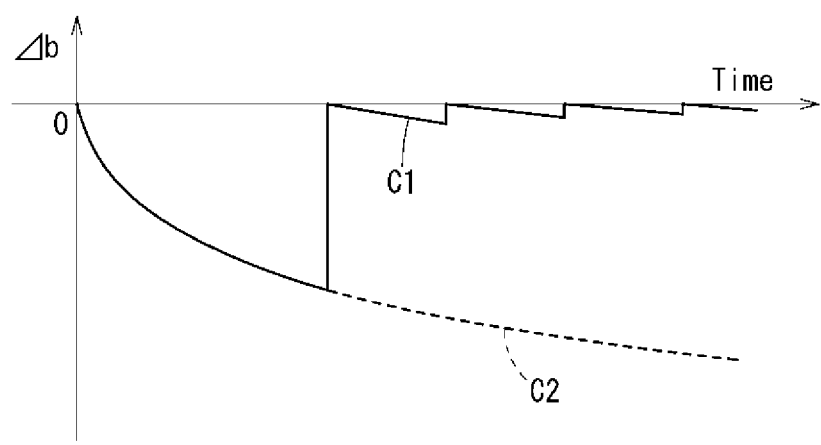
FIG. 13 is a diagram for explaining a temporal change in the reaction force for a case in which a zero reset process is performed, and a case in which the zero reset process is not performed.

By performing such a zero reset process each time that the collection and returning pump 100 is stopped, the amount of change in the reaction force of the pressed soft portion 60 can be reduced, as indicated by the curve C1 in FIG. 13. More specifically, by resetting the amount of change in the reaction force of the pressed soft portion 60 to zero each time that the collection and returning pump 100 is stopped, it is possible to eliminate a continuous increase in the amount of change of the reaction force. Accordingly, the amount of change in the reaction force in one operation period of the centrifugal separation device 14 (from the start of the initial collection operation until completion of the last returning operation with respect to an individual blood donor by the centrifugal separation device 14) is extremely small, in comparison with a case in which the zero reset process is not carried out (as indicated by the curve C2 in FIG. 13).

The internal pressure computation unit 103 of the centrifugal separation device 14 shown in FIG. 1 calculates the circuit internal pressure of the cassette 28 on the basis of the detection value of the load detecting unit 88. At this time, the internal pressure computation unit 103 calculates the circuit internal pressure using a calibration curve L (see FIG. 14A, etc.), which indicates a relationship between the detection value (load) of the load detecting unit 88 and the pressure value. The internal pressure computation unit 103 retains (stores) the calibration curve L (calibration curve data). Moreover, instead of retaining the calibration curve L, the internal pressure computation unit 103 may refer to the calibration curve L by accessing an external server in which the calibration curve L is stored.

Figure 14A:
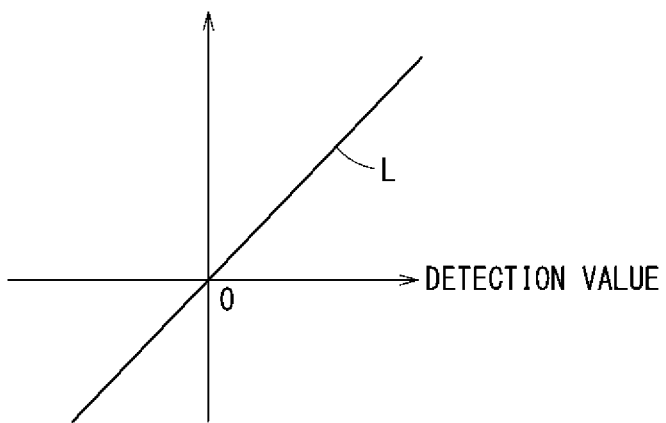
FIG. 14A is a first explanatory diagram showing an image of the zero reset process.
Figure 14B:
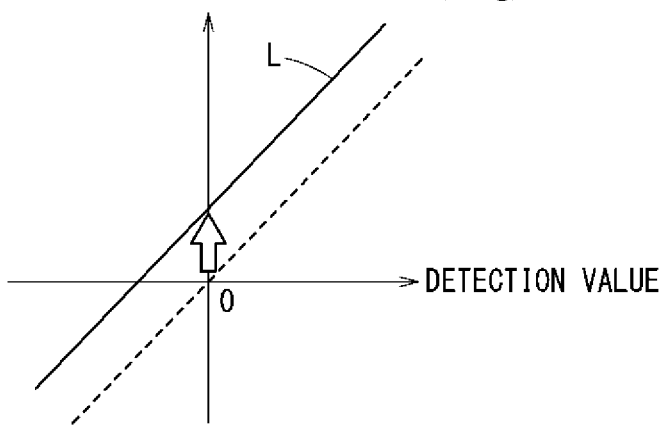
FIG. 14B is a second explanatory diagram showing an image of the zero reset process.
Figure 14C:
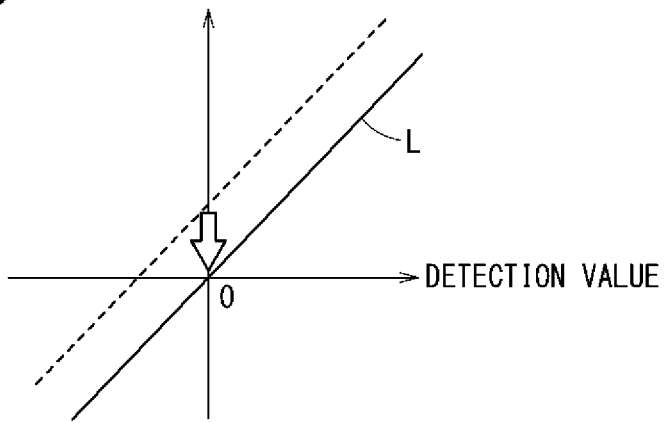
FIG. 14C is a third explanatory diagram showing an image of the zero reset process.

FIGS. 14A to 14C show images of the zero reset process. As shown in FIG. 14A, on the basis of the detection value of the load detecting unit 88 in the initial state (a state in which the amount of change in the reaction force of the pressed soft portion 60 is zero, immediately after having mounted the cassette 28 in the cassette mounting unit 78), the pressure value calculated with reference to the calibration curve L is substantially equivalent to the actual pressure value (a timewise error is not taking place). As time elapses, the reaction force of the pressed soft portion 60 with respect to the load detecting unit 88 decreases. Therefore, as shown in FIG. 14B, the calibration curve L shifts over time. As a result, in the pressure value calculated with reference to the calibration curve L, an error occurs with respect to the actual pressure value.

Thus, in the zero reset process, as shown in FIG. 14C, the calibration curve L is initialized (the portion that was shifted over time is restored), by setting the pressure value corresponding to the detection value of the load detecting unit 88, so as to become zero at each instance of the predetermined timing at which the collection and returning pump 100 is stopped. More specifically, in the circuit of the blood component collection system 10 shown in FIG. 1, when the collection and returning pump 100 is stopped, the circuit internal pressure returns to 0 mmHg within a relatively short time period (from 1 to 3 seconds). At this time, by setting the pressure value corresponding to the detection value of the load detecting unit 88 to zero, the pressure value calculated with reference to the calibration curve L is made to coincide with the actual pressure value.

The blood component collection system 10 and the circuit internal pressure acquisition method according to the present embodiment exhibit the following effects.

The cassette 28 is equipped with the pressed soft portion 60, which is pressed by the load detecting unit 88 in an attached state of being attached to the centrifugal separation device 14, and at least the pressed soft portion 60 is made of a soft material. Therefore, compared to a conventional cassette made of a hard resin the entirety of which is manufactured by injection molding, the cassette 28 can be manufactured at low cost. Further, since the pressed soft portion 60 is provided, which is pressed by the load detecting unit 88, the circuit internal pressure can be measured on the basis of the load detected by the load detecting unit 88 of the centrifugal separation device 14.

The flow path 42 of the cassette 28 is disposed inside a sheet-shaped cassette body 40 made of a soft material. In accordance with such a configuration, compared to a conventional cassette made of a hard resin and manufactured by injection molding, the cassette can be manufactured at low cost. Accordingly, with a simple and economical configuration, it is possible to measure the circuit internal pressure of the cassette 28.

According to the blood component collection system 10, the zero reset process (initialization) is performed to set the pressure value corresponding to the detection value of the load detecting unit 88, so as to become zero at each instance of the predetermined timing at which the collection and returning pump 100 is stopped. Therefore, it is possible to enhance the measurement accuracy of the circuit internal pressure. More specifically, although the reaction force of the pressed soft portion 60 that is pressed by the load detecting unit 88 changes (decreases) over time, since the pressure value is returned to zero at each instance of the predetermined timing at which the collection and returning pump 100 is stopped, it is possible to reduce the amount of change over time in the reaction force of the pressed soft portion 60. Consequently, it is possible to reduce measurement errors due to a decrease in the reaction force over time, and to measure the circuit internal pressure with high measurement accuracy.

The internal pressure computation unit 103 performs the zero reset process while the collection and returning pump 100 is stopped in order to switch between the collection operation and the returning operation. In accordance with such a configuration, as in the present embodiment, in the case that the respective cycle times of the collection operation and the returning operation are comparatively short (for example, when the cycle times of each of the operations is on the order of 1 to 2 seconds), the zero reset process is executed at the switching timing to stop the collection and returning pump 100, and therefore the zero reset process is efficient. Further, by performing the zero reset process during a relatively short time interval, it is possible to reduce the amount of change over time in the reaction force of the pressed soft portion 60, and to measure the circuit internal pressure with higher accuracy.

Moreover, in the case that the cycle time of the collection operation is comparatively long (for example, in the case of being greater than or equal to 5 minutes), the control unit 102 may stop the collection and returning pump 100 at least one time during the period of the collection operation, and the internal pressure computation unit 103 may perform the zero reset process while stopping the collection and returning pump 100 during the period of the collection operation. In accordance with such a configuration, even in the case that the cycle time of the collection operation is comparatively long, since the zero reset process is performed at each of the predetermined time intervals, the circuit internal pressure can be accurately measured.

In the case that the collection and returning pump 100 is stopped at a predetermined timing of greater than or equal to 2 seconds, the circuit internal pressure can be reliably returned to 0 mmHg (or a pressure equivalent thereto), and therefore, the effectiveness of the zero reset process can be enhanced. Further, in the case that the collection and returning pump 100 is stopped at a predetermined timing of less than or equal to 5 seconds, it is possible to prevent the overall processing time period of the blood component collection system 10 from becoming longer than necessary.

In the above-described cassette 28, the flow path 42 is formed between the first sheet 40a and the second sheet 40b, which are formed of a soft material, however, the structure that forms the flow path 42 is not necessarily limited to such a configuration. The same is true in the case of cassette 28a to be described later. For example, within the cassette body 40, the members that form the flow path 42 may be tubes. In this case, the cassette body 40 is equipped with a first tube (first line forming member) having a flow path constituting the first line 42a, a second tube (second line forming member) having a flow path constituting the second line 42b, together with a plate-shaped cassette base portion supporting the first tube and the second tube.

The pressed soft portion 60 and the clamp action member 76a are provided in the first tube. The clamp action members 76b, 76c are provided in the second tube. The cassette base part is formed so that the pressed soft portion 60 is exposed, in a manner so that the load detecting unit 88 can press on the pressed soft portion 60. Further, the cassette base portion is formed with the clamp action members 76a to 76c being exposed, in a manner so that the clamps 72a to 72c can press on the clamp action members 76a to 76c.

The biological component collection device 27 is not limited to being in the form of the cassette 28 (or the cassette 28a to be described later). Accordingly, the biological component collection device 27 may be equipped with a first soft tube member having the first line 42a, and a second soft tube member having the second line 42b, and may be constituted in a manner so that both end portions of the first soft tube member and the second soft tube member are connected together respectively via connectors.

Figure 15:
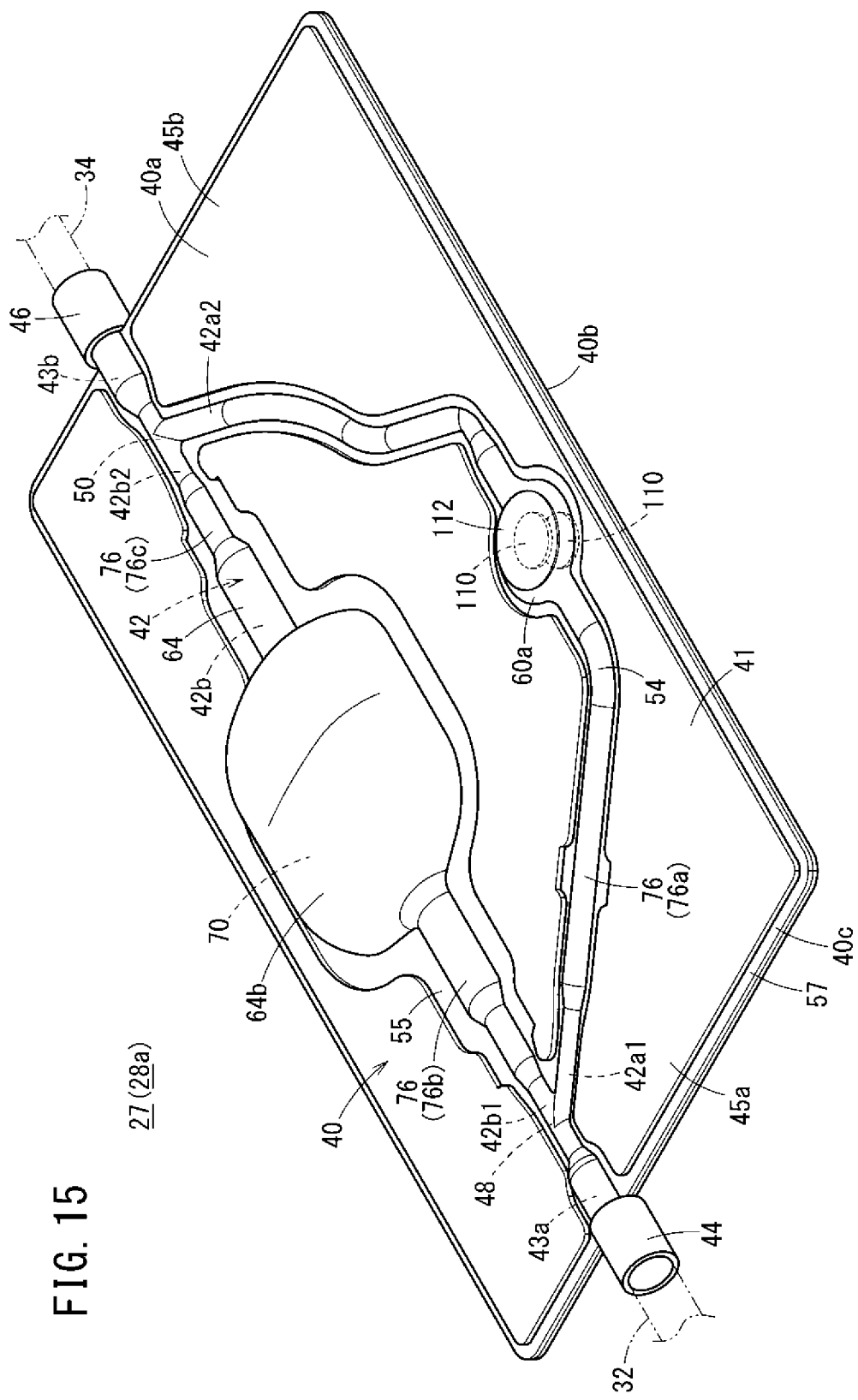
FIG. 15 is a perspective view of a biological component collection device according to another embodiment.

As another embodiment of the biological component collection device 27, the cassette 28a shown in FIG. 15 may be adopted. In the cassette 28a, a pressed soft portion 60a has a width wider than other parts in the first line forming member 54, and has a circular shape as viewed in plan in the thickness direction of the cassette 28a. A metal plate 110 is arranged on the top of the pressed soft portion 60a at each of one and the other surfaces of the cassette 28a. The metal plate 110 is, for example, made of stainless steel. Although not illustrated in detail, a recess is formed on the top of the pressed soft portion 60a and recessed toward the center of the cassette 28a in the thickness direction. The metal plate 110 is placed in the recess. A thin resin sheet 112 covering the metal plate 110 is joined to the top of the pressed soft portion 60a. The metal plate 110 may be replaced with a magnet.

Figure 16:
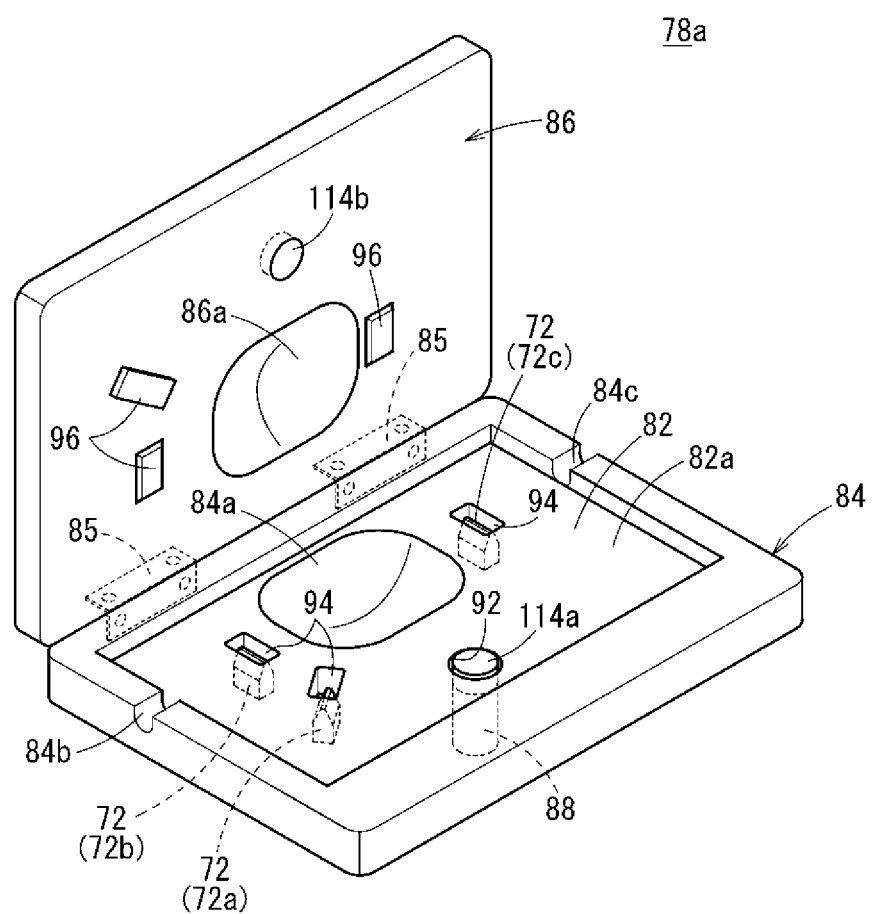
FIG. 16 a perspective view of a cassette mounting unit according to another embodiment.

The cassette 28a thus configured is attached to the cassette mounting unit 78a shown in FIG. 16. In the cassette mounting unit 78a, a magnet 114a is fixed to the tip end of the load detecting unit 88. Another magnet 114b is fixed to the lid 86 at such a location that the magnet 114b faces the magnet 114a when the lid 86 is closed. When the lid 86 is closed with the cassette 28a being held by the cassette mounting unit 78a, the cassette 28a is put into the state of being attached to the cassette mounting unit 78a. In this state, the two metal plates 110 arranged on the pressed soft portion 60a of the cassette 28a are magnetically coupled respectively to the magnets 114a, 114b fixed to the cassette mounting unit 78a. In this manner, it becomes possible to detect a load applied from the pressed soft portion 60a to the load detecting unit 88 so as to measure the circuit internal pressure of the cassette 28a.

The scope of application of the present invention is not limited to a blood component collection system 10, but may be applied to various systems through which a liquid is made to flow through a flow path, for example, a whole blood donation system, or a culture apparatus for various types of cells which are collected or cultured from patients or donors, or alternatively, a medicinal solution administration system, or the like. Accordingly, the liquid that flows in the biological component collection device (biological component collection system) is not limited to blood.

The present invention is not limited to the above-described embodiments, and various modifications may be adopted within a range that does not depart from the essence and gist of the present invention.

The invention claimed is:

1. A biological component collection system, comprising:
   a separation device having a load detector, and adapted to separate a biological component from a liquid containing at least one biological component; and
   a biological component collection device configured to be attachable to the separation device and having a flow path formed in an interior thereof;
   wherein the biological component collection device comprises a pressed soft portion forming one part of the flow path, and which is pressed by the load detector in order to measure an internal pressure of the flow path when the separation device is in operation,
   wherein the separation device comprises:
      a collection and returning pump; and
      a control unit including an internal pressure computation unit configured to:

calculates a circuit internal pressure of the biological component collection device based on a detection value of the load detector; and perform a zero reset process that includes setting a pressure value corresponding to the detection value of the load detector to zero each time the pump is stopped.

2. The biological component collection system according to claim 1, wherein:

the separation device performs a collection operation of collecting, in the biological component collection device, the liquid containing the at least one biological component from a donor, and performs a returning operation of returning an unnecessary biological component to the donor; and the internal pressure computation unit performs the zero reset process while the pump is stopped when switching between the collection operation and the returning operation.

3. The biological component collection system according to claim 1, wherein:

the separation device performs a collection operation of collecting, in the biological component collection device, the liquid containing the at least one biological component from a donor;

the control unit stops the pump at least one time during a period of the collection operation; and the internal pressure computation unit performs the zero reset process while the pump is stopped during the period of the collection operation.

4. The biological component collection system according to claim 1, wherein a time during which the pump is stopped is greater than or equal to 2 seconds.

5. The biological component collection system according to claim 4, wherein the time during which the pump is stopped is less than or equal to 5 seconds.

6. A circuit internal pressure acquisition method for measuring a circuit internal pressure of a biological component collection device with a flow path formed in an interior thereof, the biological component collection device being attached to a separation device having a load detector, the separation device being adapted to separate a biological component from a liquid containing at least one biological component;

wherein the biological component collection device comprises a pressed soft portion forming one part of the flow path which is pressed by the load detector in order to measure an internal pressure of the flow path, the circuit internal pressure acquisition method comprising:

calculating a circuit internal pressure of the biological component collection device based on a detection value of the load detector; and performing a zero reset process to set a pressure value corresponding to the detection value of the load detector, to zero when a pump of the separation device is stopped.

7. The circuit internal pressure acquisition method according to claim 6, further comprising:

performing a collection operation that includes collecting, in the biological component collection device, the liquid containing the at least one biological component from a donor, and performing a returning operation of returning an unnecessary biological component to the donor, wherein the zero reset process is performed while the pump is stopped in order to switch between the collection operation and the returning operation.

8. The biological component collection system according to claim 2, wherein a time during which the pump is stopped tit the is greater than or equal to 2 seconds.

9. The biological component collection system according to claim 8, wherein the time during which the pump is stopped is less than or equal to 5 seconds.

10. The biological component collection system according to claim 3, wherein a time during which the pump is stopped is greater than or equal to 2 seconds.

11. The biological component collection system according to claim 10, wherein the time during which the pump is stopped is less than or equal to 5 seconds.

12. The circuit internal pressure acquisition method according to claim 6, further comprising:

performing a collection operation that includes collecting, in the biological component collection device, the liquid containing the at least one biological component, wherein the zero reset process is performed at least one time during the collection operation while the pump is stopped.

13. The circuit internal pressure acquisition method according to claim 6, wherein a time during which the pump is stopped is greater than or equal to 2 seconds.

14. The circuit internal pressure acquisition method according to claim 13, wherein the time during which the pump is stopped is less than or equal to 5 seconds.

15. The circuit internal pressure acquisition method according to claim 7, wherein a time during which the pump is stopped is greater than or equal to 2 seconds.

16. The circuit internal pressure acquisition method according to claim 15, wherein the time during which the pump is stopped is less than or equal to 5 seconds.

* * * * *